United States Patent [19]
Papakostopoulos

[11] Patent Number: 5,838,423
[45] Date of Patent: Nov. 17, 1998

[54] APPARATUS FOR COLLECTING DATA

[75] Inventor: Demetrius Papakostopoulos, Redland, United Kingdom

[73] Assignee: Atel Systems Limited, United Kingdom

[21] Appl. No.: 535,202

[22] PCT Filed: Apr. 26, 1994

[86] PCT No.: PCT/GB94/00883

§ 371 Date: Apr. 4, 1996

§ 102(e) Date: Apr. 4, 1996

[87] PCT Pub. No.: WO94/24926

PCT Pub. Date: Nov. 10, 1994

[30]     Foreign Application Priority Data

Apr. 29, 1993  [GB]  United Kingdom ................ 9308893

[51] Int. Cl.⁶ ............................................. A61B 3/02
[52] U.S. Cl. ............................ 351/242; 377/13; 434/81
[58] Field of Search .................... 351/242, 222, 351/200; 377/13, 17, 27, 28, 37, 38, 55; 434/81, 238

[56]        References Cited

U.S. PATENT DOCUMENTS 3,609,740   9/1971  Paine et al. ............................. 351/242
3,807,838   4/1974  Meyers ..................................... 351/42
4,239,958  12/1980  Pritty ...................................... 434/238

*Primary Examiner*—Huy Mai
*Attorney, Agent, or Firm*—Larson & Taylor

[57]        ABSTRACT

An apparatus is provided for collecting data. The apparatus is particularly, but not exclusively, applicable for the diagnosing of eye disorders. The apparatus contains a rack (1) having a plurality of engagement positions and a plurality of counters (5) for the rack (1), each counter (5) being engageable in any one of the engagement positions. Each counter (5) contains a specific, unique, electrical attribute which enables a detector included within the apparatus to detect and therefore process the data relating to the value of the electrical attribute of each counter (5).

14 Claims, 4 Drawing Sheets

APPARATUS FOR COLLECTING DATA

BACKGROUND OF THE INVENTION

1. Field of the Invention

The present invention relates to an apparatus for collecting data. It is particularly, but not exclusively, applicable for the diagnosing of eye disorders.

2. Summary of the Prior Art

A method for determining the ability of a person to distinguish between different colors is known wherein one or more racks each containing a plurality of colored counters is provided, each counter having a different color to each of the other counters such that when the counters are arranged linearly in their correct order the color of each counter except the first differs slightly and progressively from that of the preceding counter. It is the task of the subject of the test to arrange the counters in their correct order in the or each rack, relying only on the color of each counter.

In the known method, each counter is numbered on the underside. The process of collecting and processing the data involves noting the order of the counters according to their numbers and then calculating the ability of the subject to distinguish colors based on these numbers according to known algorithms. The results of these computations are usually plotted on a circular graph for interpretation.

The ability of the subject to distinguish between colors can be determined using four racks, each containing twenty-two counters. This involves eighty-five different colors, the last counter of each rack having the same color as the first counter of the next rack.

The collection and processing of the data in this way is a time-consuming activity, typically taking about 2½ hours.

SUMMARY OF THE INVENTION

The present invention seeks to provide an apparatus for carrying out the collection of the data electrically. The data can then be easily and rapidly processed electronically.

At its most general, the present invention proposes that the numbering of the counters in the known method described above is replaced by the assignment to each counter of a specific electrical attribute, such as resistance. Then, means are provided for measuring the electrical attributes of the counters when they are arrayed in a rack, and processing that measurement of counter information to derive an analysis of the arrangement of the colors of the counters.

Accordingly, a first aspect of the present invention may provide an apparatus for collecting data comprising a rack having a plurality of engagement positions, a plurality of counters for the rack, each counter being engageable in any one of the engagement positions;

wherein:
each of the counters has a specific electrical attribute, the value of the electrical attribute of each counter differing from that of each of the other counters; and
the apparatus further includes detection means for detecting the value of the electrical attribute of each counter when engaged in corresponding engagement positions and processing means for collecting and processing the data relating to the value of the electrical attribute of each counter.

In the event that the apparatus is used for diagnosing eye conditions, each counter may have a colored portion, the color of the colored portion of each counter differing from the color of the colored portion of each of the other counters. The subject of the diagnostic test must arrange the counters in color order in the rack. There may be a plurality of racks with the counters having different colors. Then, either all the counters have a different value of the electrical attribute, or the counters within each rack have a different value, and there is also means for distinguishing each rack.

The electrical attribute most conveniently used in the present invention is resistance. If resistance is the electrical attribute used, each engagement position preferably has a hole and the detecting means includes electrical contacts for contacting the portion of specified electrical resistance of each counter through the corresponding hole. In this case the detecting means includes means for measuring the electrical resistance of the portion of specified electrical resistance of each counter.

The processing means processes the data relating to the value of the electrical attribute of each counter so that it may then determine the ability of the test subject to distinguish between colors.

It should be noted that the present invention does not relate solely to an apparatus for collecting data as discussed above. In addition, a second aspect of the present invention provides an assembly of a plurality of counters and a rack for housing the plurality of counters, the rack having a base and a lid hinged together by hinges; wherein the internal walls of the rack are substantially equal to the height of the counters and there are a plurality of holes corresponding to the plurality of counters in the base for receiving its counters.

In this aspect, the shaping of the rack holds the counters firmly in place, when the lid is closed on the base, so that the subject of the diagnostic test can arrange the counters in order, and the person giving the test can then close the rack and transport the rack without the risk of the counters changing position.

In a third aspect of the present invention there is provided a set of counters, each counter having a circular upper and lower surface;

wherein:
that the lower surface provides an electrical attribute differing from the electrical attribute of each of the other counters.

As previously mentioned in order to carry out the full diagnostic test, there may be a plurality of racks. Hence, a fourth aspect of the present invention may provided a system for collecting data comprising:

a data collecting probe having a platform with a first recess, a cover with a second recess being hinged along one side to the platform by hinges, contact in the recess of the cover being connected to a processing means; and a plurality of racks selectively and interchangeably insertable into the data collecting probe such that any one of the plurality of racks is receivable in the first and second recesses, each of the racks containing a plurality of counters, the contacts being arranged to contact respective counters when the corresponding rack is received in the probe and the processing means is arranged to collect and process data relating to said counters.

BRIEF DESCRIPTION OF DRAWINGS

An embodiment of the present invention is described in detail, by way of example, with reference to the accompanying drawings, in which.

DETAILED DESCRIPTION

Figure 1:
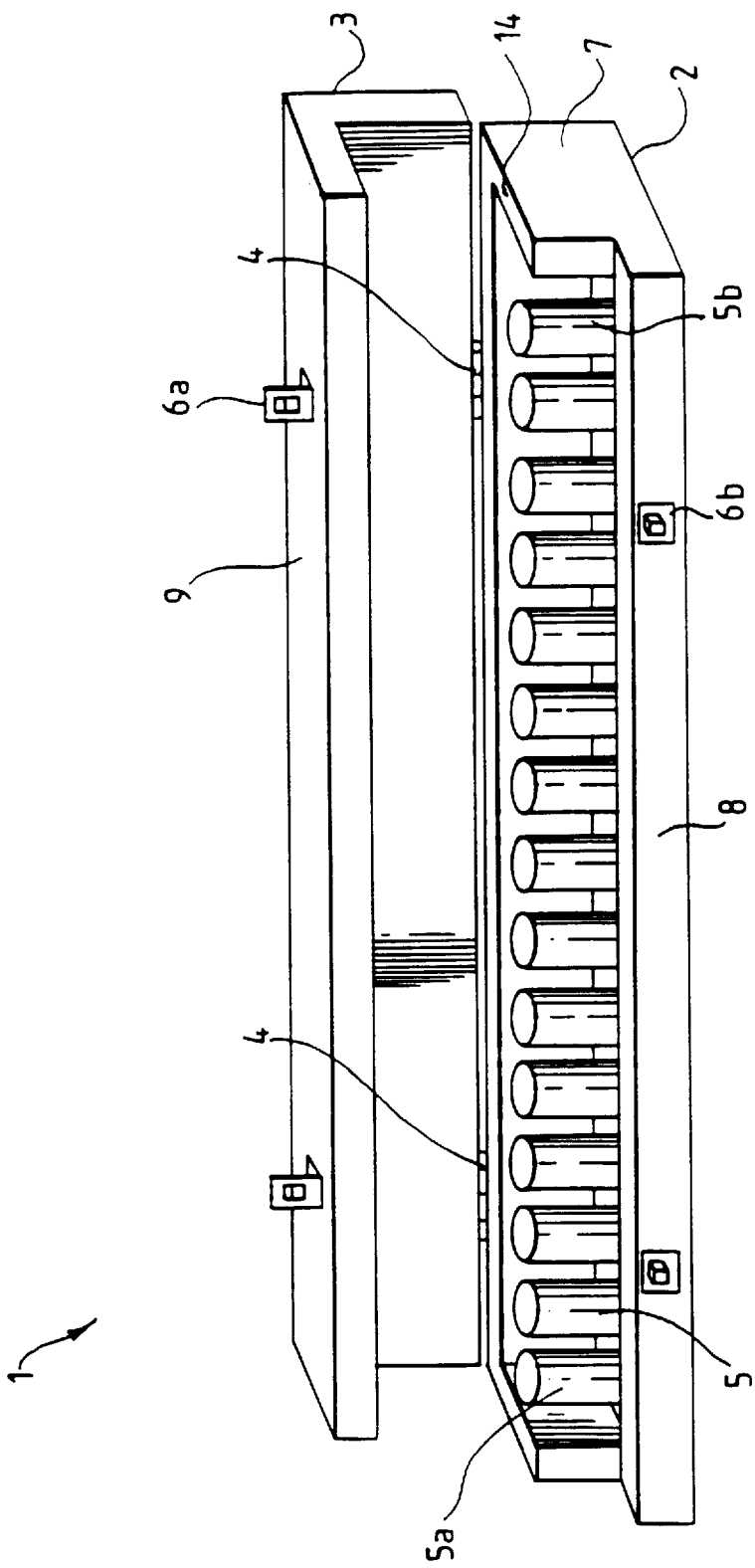
FIG. 1 is a perspective view of a rack used in the present invention.
Figure 2:
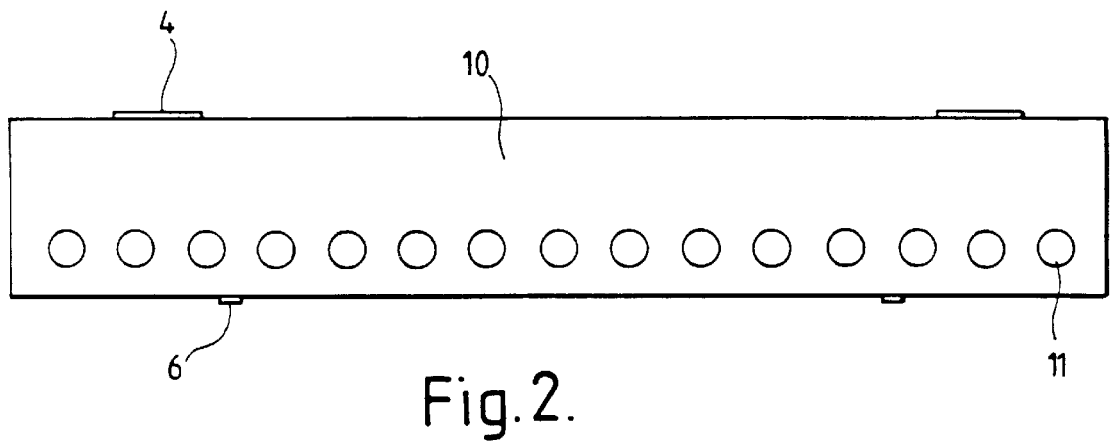
FIG. 2 is a plan view of the rack of FIG. 1.
Figure 3:
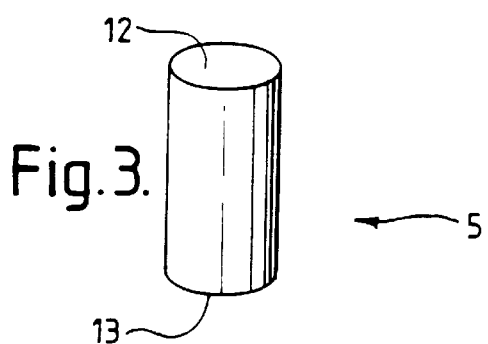
FIG. 3 is a perspective view of a counter used in the rack of FIG. 1.
Figure 4:
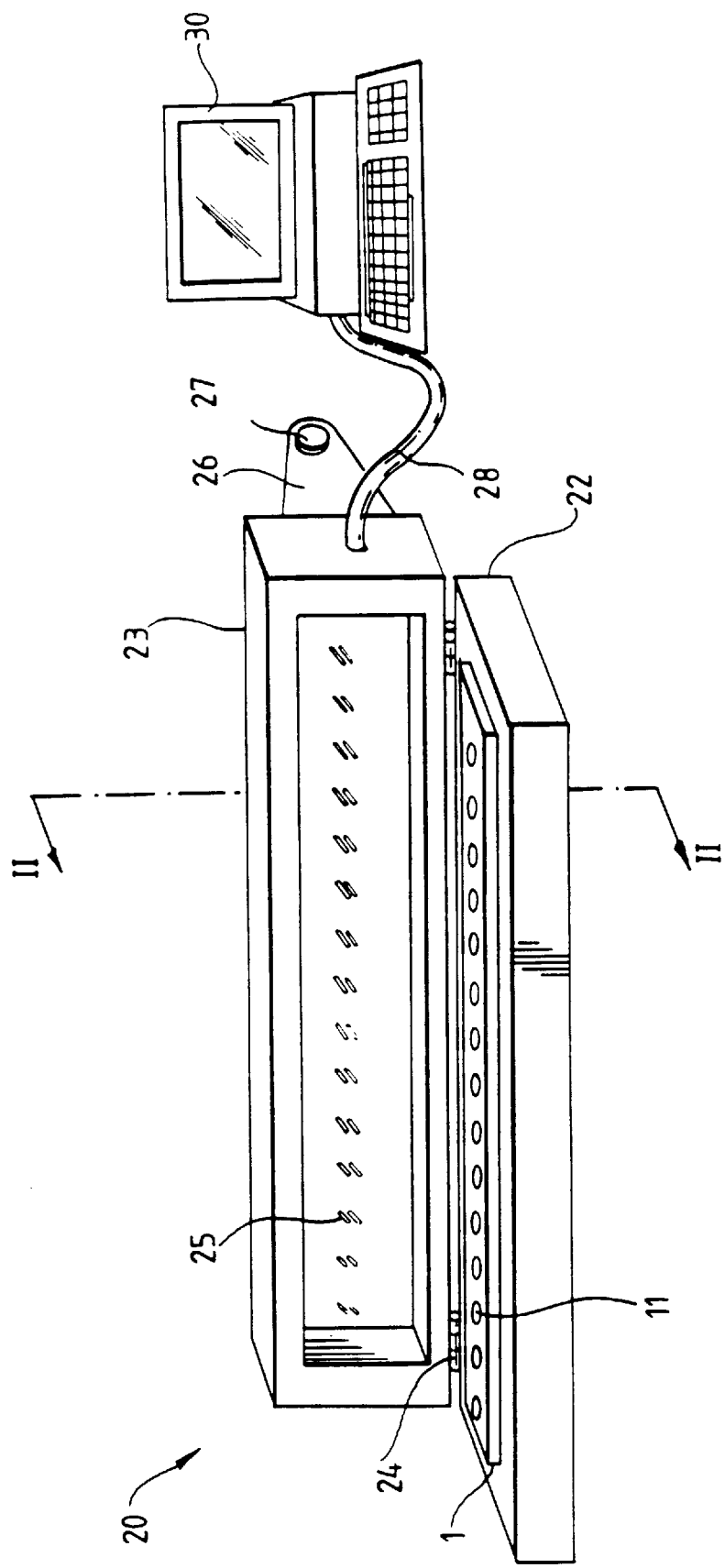
FIG. 4 is a perspective view of a data collection probe which receives the rack of FIG. 1.
Figure 5:
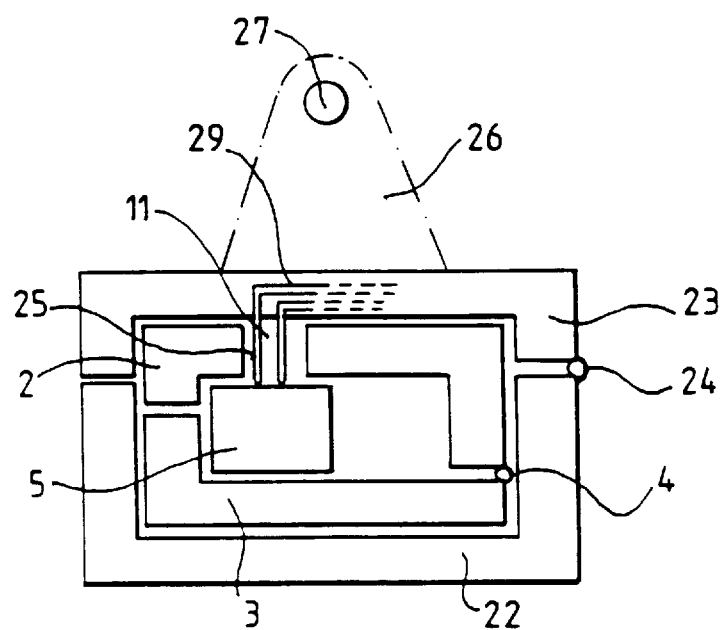
FIG. 5 is a sectional view along line II—II in FIG. 4.

The apparatus comprises a rack 1 in which colored counters 5 may be arranged and a data collection probe 20 into which the rack 1 is placed to determine the order of the counters 5. The rack 1 has a base 2 and a lid 3 which are hinged together by hinges 4. The base has two side walls 7 which are stepped down from the edge to which the lid 3 is hinged to form a front wall 8. The front wall 8 is lower than the side walls 7 in order to facilitate the insertion into and removal from the rack of counters 5 which have a height substantially equal to that of the internal surface of the side walls 7. Female catch members 6b,6a are attached to the front wall 9 of the lid 3 and male catch members 6b are attached to the front wall 8 of the base 2. The male and female catch members 6a, 6b can engage with each other to secure the rack in a closed condition.

The counters 5 may be positioned in the rack over holes 11 formed in the floor 10 of the rack base 2. The lower surface 13 of each counter 5 may have a protrusion in the form of a locating ring, or each hole 11 may have a recess around its upper edge to ensure proper positioning of each counter 5 over a hole. There are the same number of counters 5 as there are holes 11.

The lid 3 can only close over the base 2 with engagement of the catches 6 when the counters 5 are properly positioned over the holes 11. Since the height of each counter 5 is substantially equal to the height of the inside surface of the side wall 7, and the lid 3 in its closed condition lies flush with the top surface 14 of the side wall 7, closure of the lid and engagement of the catches 6 holds the counters securely in their positions over the holes 11. The end counters 5a and 5b are fixed in the rack 1.

Each counter 5 has a circular upper surface 12, most or all of which is colored. When the counters are arranged in their correct order, the color of each counter except the first differs slightly and progressively from that of the preceding counter. Each counter 5 also has a circular lower surface 13 coated with a material having a resistivity different from that of each of the materials coating the lower surface 13 of each of the other counters 5 in the rack.

The subject of the test arranges the counters 5 in the rack 1 in the order in which he/she considers that the color progress in sequence from the fixed counter 5a to the fixed counter 5b. The lid 3 is then closed and the catches 6 engaged. The rack 1 is then turned upside down and inserted into a recess formed in the platform 22 of a data collection probe 20. The data collection probe 20 has a platform 22 with a recess for receiving a rack 1. The platform 22 is hinged along one side to a cover 23 with hinges 24. A rod-shaped handle 27 is attached to the top surface of the cover 23 by stands 26. A recess is formed in the cover 23 to accommodate the part of the rack 1 which protrudes from the recess in the platform 22 when the cover is swung down over the rack 1. Pairs of electrical contacts 25 are arranged in the recess in the cover 23 such that when the cover 23 is swung down over the platform 22, each pair of contacts 25 protrudes through a hole 11 in the rack base 2 and forms an electrical contact with the lower surface 13 of a counter 5. The spacing between the tips of the contacts in each pair is equal for all pairs of contacts. There are as many pairs of electrical contacts 25 as there are holes 11. Wires 29 pass through the cover 23 and are bundled together into a lead 28, which leads to a processing means in the form of a computer 30 which analyses and processes the data collected by the probe 20. Voltage is applied to each pair of contacts 25 thought the wires 29 to determine the resistivity of the material coating the lower surface 13 of each counter 5.

The computer 30 is then able to determine the order of the counters 5 in the rack 1 since the resistivity of the lower surface 13 of each counter 5 uniquely identifies the color of that counter and therefore determines its correct position in the rack. The computer 30 can them process the data obtained by the probe 20 to determine the ability of the subject to distinguish colors. Preferably, four racks are provided, each having a different range of colors and the fixed counter 5a of each rack having a lower surface of different resistivity to enable the computer to identify which rack is which.

Safeguards may be built into the computer program for processing the data obtained by the probe. For instance, the computer 30 can refuse to accept incomplete sets of data e.g. if one or more counters are missing from the rack, if one or more counters has been placed in the rack upside-down, if one or more counters is not properly in position over a hole 11.

It will be understood that the present invention is not limited to the aforementioned embodiment. Variations will be apparent to the person skilled in the art e.g. different electrical attribute such as voltage, inductance, capacitance etc.

The present invention provides an apparatus for carrying out a collection of data electrically. It is particularly applicable for diagnosing brain conditions which result in eye disorders. The apparatus provides a simple way for the patient to be tested along with a quick provision of corresponding data. It is also possible due to special features of the rack and probe that once the test has been completed the rack can be closed thereby immobilising the counters and allowing the analysis to be done at a later date or after several other racks have been analysed. Several racks may be provided each containing counters covering a different range of colors per data collection probe.

Although the diagnosis of eye disorders would be the most obvious application of the present invention, it would be possible with only a few modifications to provide an educational tool, or child's educational toy for such things as spellings.

I claim:

1. An apparatus for collecting data comprising:

at least one rack, said at least one rack containing a plurality of counters, each counter having an associated electrical attribute of a known value, of the electrical attribute of each counter differing from that of each of the other counters of said at least one rack; and processing means for collecting and processing data; relating to the electrical attributes said counters the apparatus further comprising a data collecting probe having a platform including a first recess, a cover including a second recess and having hinges along one side for connecting the cover to the platform, contacts disposed in the recess of the cover and connected to said processing means, the contacts being arranged to contact respective counters when said at least one rack is received in the probe, and said at least one rack being insertable into the data collecting probe so as to be received in the first and second recesses.

2. An apparatus according to claim 1, wherein said at least one rack has a plurality of engagement positions for receiving and engaging the plurality of counters, each counter being engageable in any one of the engagement positions.

3. An apparatus according in claim 2 wherein each engagement position comprises a through-passage and the contacts contact a respective counter through the corresponding through-passage.

4. An apparatus according to claim 3, wherein the through-passages are in a line.

5. An apparatus according to claim 3, wherein the through-passages from a plurality of parallel lines.

6. An apparatus according to claim 1, wherein said counters have a common height and wherein said at least one rack comprises a base, a lid including hinges for connecting the lid to the base, and internal walls, said internal walls being of height substantially equal to the common height of the counters.

7. A apparatus according to claim 6, wherein the lid and base have female catch members and male catch members, respectively, said catch members being engageable with each other to thereby secure the counters in a fixed position within the rack.

8. An apparatus according to claim 1, wherein the contacts are arranged in pairs.

9. An apparatus according to claim 8 wherein the contacts have tips with a spacing therebetween and the spacing is equal for all of said pairs of contacts.

10. An apparatus according to claim 8, wherein the pairs of electrical contacts are equal in number to the through-passages.

11. An apparatus according to claim 1 wherein each counter has a colored portion having a predetermined color, the color of the colored portion of each counter of said at least one rack differing from the color of the colored portion of each of the other counters of said at least one rack.

12. An apparatus according to claim 1 wherein the plurality of counters for said at least one rack varying in color across a range of different colors.

13. An apparatus according to claim 1 wherein the specific electrical attribute comprises is resistance.

14. An apparatus according to claim 1 in which said at least one rack comprises a plurality of racks, and the racks are selectively and interchangeably insertable into the data collecting probe.

\* \* \* \* \*